United States Patent [19]

Won

[11] Patent Number: 5,201,330
[45] Date of Patent: Apr. 13, 1993

[54] DENTAL FLOSS HOLDER

[76] Inventor: Se K. Won, 6261 Glacier Dr., Westminster, Calif. 92683

[21] Appl. No.: 911,963

[22] Filed: Jul. 10, 1992

[51] Int. Cl.$^5$ .............................................. A61C 15/00
[52] U.S. Cl. ...................................... 132/325; 132/324
[58] Field of Search ............... 132/323, 324, 325, 327, 132/328

[56] References Cited

U.S. PATENT DOCUMENTS

| | | | |
|---|---|---|---|
| 4,254,786 | 3/1981 | Won | 132/325 |
| 4,574,823 | 3/1986 | Uriss | 132/325 |
| 5,038,806 | 8/1991 | Ewald | 132/325 |

OTHER PUBLICATIONS

Product Mounting Card, Se Won Industry (1983).

*Primary Examiner*—Robert P. Swiatek
*Assistant Examiner*—Cindy A. Cherichetti
*Attorney, Agent, or Firm*—Robert R. Thornton

[57] ABSTRACT

A dental floss holder is provided with a slot-headed locking axle on which a spool of floss is mounted. A length of floss from the spool disposed within the holder passes through the axle slot and is spanned across two spaced prongs formed on the holder and locked to the axle by being wound on the axle beneath the slotted head after spanning. Tension is applied to the spanned floss by rotating a locking flange which is held in position by the slotted head of the locking axle to provide a taut span of floss which can be manipulated between the user's teeth.

2 Claims, 1 Drawing Sheet

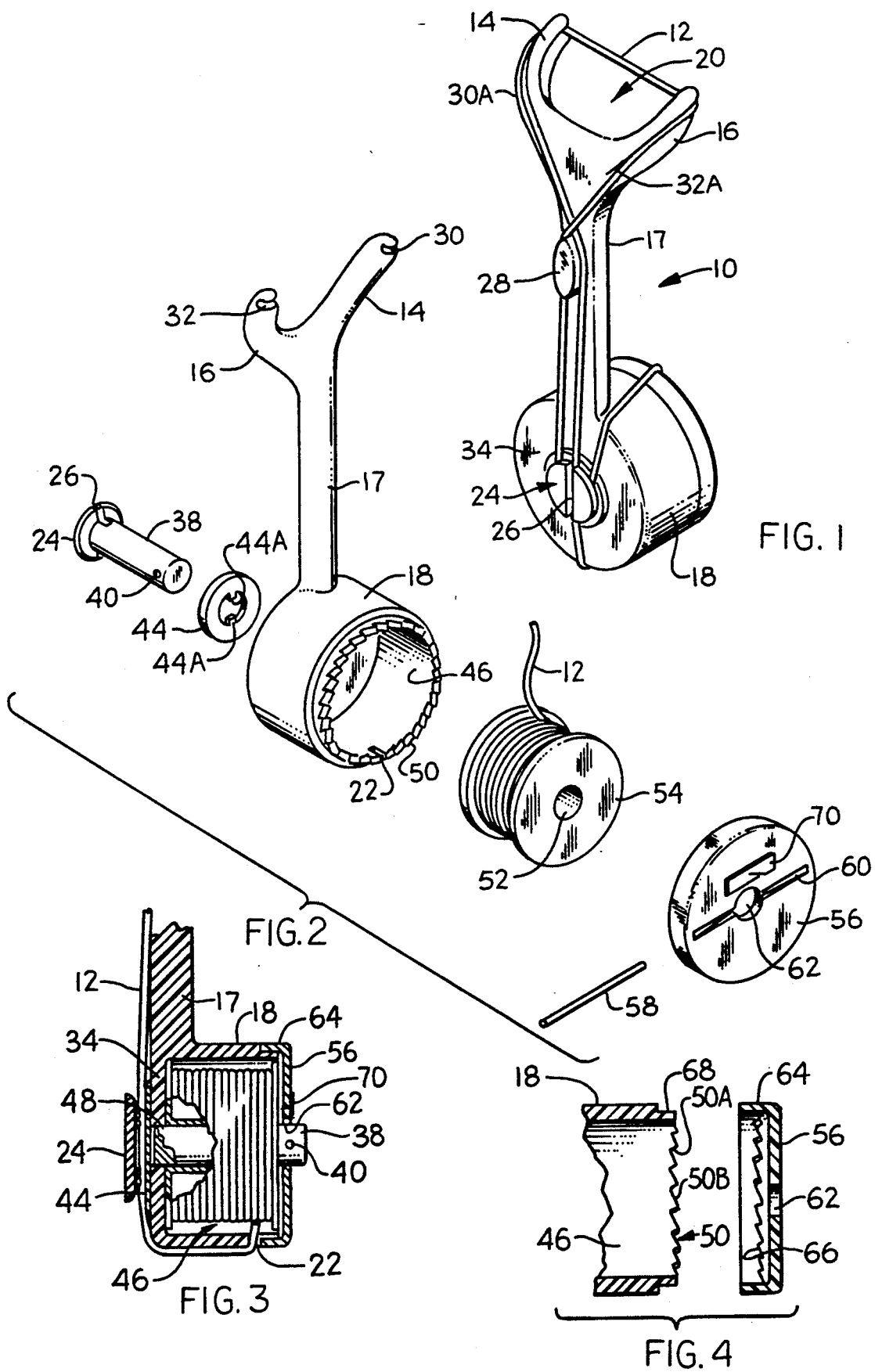

DENTAL FLOSS HOLDER

BRIEF DESCRIPTION OF THE INVENTION

This invention relates to a dental floss holder containing a supply of floss and adapted to provide an exposed section of dental floss maintained under tension for cleaning between the user's teeth and is an improvement of the Dental Floss Holder shown in my prior U.S. Pat. No. 4,254,786, issued Mar. 10, 1981.

In the holder described in U.S. Pat. No. 4,254,786, a length of floss wound on a spool is held within a body member is manually pulled from the spool. When a sufficient length has been unwound, the floss is wound about one side of a slotted head on a locking axle, threaded over two prongs on the holder, and wound about the other side of the slotted head. The locking axle is fixed in position by means of a ratcheting spring clip which engages ratcheting recesses formed in the bottom of the body member. Tension is applied to the floss when stretched between the two prongs by rotation of the locking axle. The taut floss can be manipulated between teeth when the holder is held by the user. However, in use, because of the strength of the spring, removal of the spring when it is necessary to replace the spool of floss has been extremely difficult, resulting in user dissatisfaction.

In the present invention, the ratcheting spring clip is replaced by a locking flange having a series of complementary ratcheting recesses formed within a depending lip on the periphery of the flange, so that each of the ratcheting recesses on the body member engages a complementary ratcheting recess on the locking flange to unidirectionally lock the flange against the body member. A diametrial groove is formed on the exterior surface of the locking flange so as to extend through an aperture in the flange which mounts the flange on the axle. A transverse passageway in the axle contains a pin which is disposed in the groove so as to urge the locking flange against the body member, by slightly loading the pin in deflection. A floss cutter is disposed on the face of the flange so as to be located adjacent the axle.

BRIEF DESCRIPTION OF THE DRAWING

The invention may be more readily understood by referring to the accompanying drawing, in which:

FIG. 1 is a perspective view of a dental floss holder according to the present invention;

FIG. 2 is an exploded perspective view thereof;

FIG. 3 is a side elevational view, partly in section, thereof; and

FIG. 4 is a fragmentary sectional view of a portion of the holder ratcheting mechanism.

DETAILED DESCRIPTION OF THE PREFERRED EMBODIMENT

Referring now to FIG. 1, there is shown a perspective view of a dental floss holder illustrating the manner in which dental floss is spanned between the first prong 14 and a second prong of the holder. The holder 10 has a body portion 18 which is generally cylindrical and to which the prongs 14 and 16 are connected by a stem 17 so as to be in a "wishbone" disposition and generally normal to the main body 18. A space 20 is formed between the prongs 14, 16 to provide an access way to the spanned floss 12 in order to assist in the flossing operation. A slot 22 (not shown, see FIG. 2) is formed in the body portion 18 opposite the stem 17 to provide a passageway through which the floss 12 emerges from within the body portion 18. As is seen in FIG. 1, the floss 12 passes from the main body portion 18 over a slotted head portion 24 of an axle 38 (see FIG. 2) through a slot 26 formed therein. Then, the floss passes around a floss separator boss 28 formed on the stem 17 and is guided onto the prong 14 and around a prong tip slot 30 (see FIG. 2) by a deep slot 30A. The floss 12 then passes to a similar tip slot 32 formed on the second prong 16. From the tip slot 32, the floss passes through a deep slot 32A formed in the second prong 16 to the floss separator boss 28 on the stem 17 and then to and under the slotted head 24, and around the axle 38, about which the floss 12 is tightly wound, preferably twice, in order to lock the floss between the slotted head 24 and a slotted washer 44 (see FIG. 3) which is held against the main body portion 18 at a generally closed face 34 formed thereon.

Referring now to FIG. 2, the axle 38 which terminates in the slotted head 24 at one end and, at the other end, has a transverse passageway 40 formed therein. A slotted washer 44 is mounted on the axle 38 adjacent the slotted head 24 by a pair of teeth 44A which engage the slot 26 so as to permit limited axial movement relative between the washer 44 and the slotted head 24. The floss passes around the axle 38 and is clamped between the slotted head 24 and the washer 44. The body portion 18 has a central axial bore 46 formed therein which terminates in a small aperture 48 (see FIG. 3), formed in the generally enclosed face 34 so as to be axially aligned with the central bore 46. At its opposite end, the axial bore 46 opens on to a series of ratcheting recesses 50 formed about the periphery of the body portion 18 opposite the generally closed face 34.

A spool 54 holding the floss 12 is adapted to fit within the axial bore 46. The spool is inserted within the bore 46 so that the axle 38 extends through a central bore 52 in the spool. A locking flange 56 encloses the spool 54 within the bore 46. A locking pin 58 is disposed in a diametrial recess 60 formed in the outer face of the locking flange 56 so as to extend across a bore 62 formed in the locking flange 56. The axle 38 extends through the bore 62 (see FIG. 3). The diametrial recess 60 varies in depth along its length, having the greatest depth at the bore 62 and lessening in depth as the recess 60 extends toward the periphery of the locking flange 56. Thus, the locking pin, when disposed in the diametrial recess 60 so as to extend through the transverse passageway 40 on the axle 38 is deflected inwardly toward the axial bore 46, thereby holding the locking flange 56 snugly against the main body portion 18.

As is seen in FIG. 4, the ratcheting recesses 50 on the main body portion 18 are unidirectional in nature, that is, each recess 50 has a stop face 58 and a deflection face 50B. The locking flange 56 has a depending lip 64 around the periphery thereof. Immediately within the depending lip 64 is a circular shoulder of ratcheting recesses 66 which are complementary to the ratcheting recesses 50 of the main body portion. In other words, when the shoulder ratcheting recesses 66 engage the ratcheting recesses 50, only unidirectional relative movement between the main body portion 18 and the locking flange 56 is possible. The main body portion 18 has an external shoulder 68 formed adjacent the ratcheting recesses 50 so that the locking flange 56 may be snugly mounted on the main body portion 18 by means of the depending lip 64 enclosing the shoulder 68.

Referring back to FIG. 3, floss holder 10 is shown partially in section, illustrating the means by which the floss 12 is passed from the axial bore 46 around the axle 38 between the slotted head 34 and the washer 44, and from underneath the slotted head 34 to the prongs 14, 16 and back to the slotted head 34, as is shown in FIG. 1. The floss end representing any excess floss after wrapping around the axle 38, is then brought to the face of the locking flange 56 and cut off by means of a cutter blade assembly 70. When it is desired to increase the tension on the floss 12 spanned between the prongs 14 and 16, the locking flange 58 is rotated manually so as to increase the tension on the floss 12 in the slot 26.

The dental floss holder 10 of the present invention employs a simple locking arrangement to enable the user to readily lock the spanned floss, thereby permitting a tensioned length of floss to be formed quickly and with a minimum of effort for immediate use. In use, the holder 10 is partially inserted into the mouth of the user so that the prongs 14, 16 are disposed, one to the lingual and one to the labial side of the tooth structure to be cleaned. The floss 12 is then worked between adjacent teeth in order to provide the cleaning function. While the teeth are being so cleaned, increased tension may be supplied by rotation of the locking flange as previously described. When the floss has become worn, it is unwound from the slotted head 24 and new floss pulled from the spool 54 and spanned between the prongs 14, 16 and locked by means of the slotted head 24 as previously described. New floss is then available for use in cleaning additional teeth.

I claim:

1. In a dental floss holder of the type having a body member with an axial bore formed therein so as to extend from one side thereof, which is open and on which unidirectional ratcheting teeth are circularly disposed in axial alignment with the bore, to the other body side which is closed but with a small diameter opening extending therethrough, a pair of prongs extending outwardly laterally from the body member normal to the bore in a wishbone configuration, each of said prongs having a deep floss receiving groove formed longitudinally along its outer surface, and each prong terminating in a tip across which the groove extends toward the other prong, an axle extending through the body member and having a head with a slot formed on one end thereof so as to be disposed adjacent the small diameter opening and a washer mounted on the axle and fixed thereto adjacent to the slotted head by means of a pair of teeth formed on the washer inner periphery and extending into the head slot at ether end thereof, a spool for holding dental floss mounted on the axle within the body member, and a passageway formed on the body member for passing the floss from the spool through the body member, the combination of:

a locking flange of circular cross-sectional configuration having a central aperture extending therethrough adapted to receive the axle, said flange extending therethrough lip depending therefrom so as to enclose the main body ratcheting recesses when the flange is mounted on the axle, and a circular shoulder formed within the recess formed by the lip and adjacent thereto, said shoulder having ratcheting teeth formed thereon so as to be complementary to the main body ratcheting teeth and engageable therewith when the flange is mounted on the axle; and locking flange attaching means connected between said locking flange and said body member mounted for attaching said flange to said axle so as to hold said flange ratcheting means in engagement with said main body ratcheting teeth; said locking flange attaching means including a diametrical groove in the flange on the side thereof opposite the flange ratcheting teeth, said groove diminishing in depth outwardly from the central aperture, and a pin disposed in said groove so as to extend through a transverse passageway formed in said axle so that said axle holds said pin in a deflected disposition in said groove so as to urge the flange ratcheting teeth against the main body ratcheting teeth.

2. A dental floss holder according to claim 1 and including floss cutting means mounted on said locking flange on the side thereof opposite said main body ratcheting teeth.

* * * * *